United States Patent
Myung et al.

(10) Patent No.: US 7,857,849 B2
(45) Date of Patent: *Dec. 28, 2010

(54) ARTIFICIAL CORNEAL IMPLANT

(75) Inventors: David Myung, Mountain View, CA (US); Jaan Noolandi, Palo Alto, CA (US); Alan J. Smith, Redwood City, CA (US); Curtis W. Frank, Cupertino, CA (US); Christopher Ta, Saratoga, CA (US); Yin Hu, Palo Alto, CA (US); Won-Gun Koh, Seoul (KR); Michael R. Carrasco, Sunnyvale, CA (US)

(73) Assignees: The Board of Trustees of the Leland Stanford Junior Iniversity, Palo Alto, CA (US); Santa Clara University, Santa Clara, CA (US)

( * ) Notice: Subject to any disclaimer, the term of this patent is extended or adjusted under 35 U.S.C. 154(b) by 771 days.

This patent is subject to a terminal disclaimer.

(21) Appl. No.: 11/243,952

(22) Filed: Oct. 4, 2005

(65) Prior Publication Data
US 2006/0083773 A1    Apr. 20, 2006

(51) Int. Cl.
*A61F 2/14* (2006.01)
(52) U.S. Cl. ............. 623/5.16; 623/6.56; 424/427; 435/180; 351/160 H
(58) Field of Classification Search ............. 623/5.16, 623/6.56; 424/427; 435/396, 180; 351/160 H
See application file for complete search history.

(56) References Cited

U.S. PATENT DOCUMENTS

| | | | |
|---|---|---|---|
| 4,391,797 A * | 7/1983 | Folkman et al. | 424/425 |
| 4,452,925 A * | 6/1984 | Kuzma et al. | 523/106 |
| 4,487,865 A * | 12/1984 | Balazs et al. | 524/29 |
| 4,500,676 A * | 2/1985 | Balazs et al. | 428/425.1 |
| 4,536,554 A * | 8/1985 | Lim et al. | 526/264 |

(Continued)

FOREIGN PATENT DOCUMENTS

WO    WO 94/01468 A1 *    1/1994

(Continued)

OTHER PUBLICATIONS

European search report for European Application No. 05807352.9 dated Mar. 30, 2010.*

(Continued)

*Primary Examiner*—Paul Prebilic
(74) *Attorney, Agent, or Firm*—Lumen Patent Firm (57) ABSTRACT

A material that can be applied as implants designed to artificially replace or augment the cornea, such as an artificial cornea, corneal onlay, or corneal inlay (intrastromal lens) is provided. The artificial corneal implant has a double network hydrogel with a first network interpenetrated with a second network. The first network and the second network are based on biocompatible polymers. At least one of the network polymers is based on a hydrophilic polymer. The artificial cornea or implant has epithelialization promoting biomolecules that are covalently linked to the surface of the double network hydrogel using an azide-active-ester chemical linker. Corneal epithelial cells or cornea-derived cells are adhered to the biomolecules. The double network has a physiologic diffusion coefficient to allow passage of nutrients to the adhered cells.

21 Claims, 10 Drawing Sheets

U.S. PATENT DOCUMENTS

| | | | | |
|---|---|---|---|---|
| 4,693,715 | A | 9/1987 | Abel, Jr. | 623/5 |
| 4,973,493 | A * | 11/1990 | Guire | 427/2.24 |
| 4,978,352 | A | 12/1990 | Fedorov et al. | 606/166 |
| 5,030,230 | A | 7/1991 | White | 623/5 |
| 5,067,961 | A | 11/1991 | Kelman et al. | 623/5 |
| 5,087,392 | A * | 2/1992 | Burke et al. | 264/2.7 |
| 5,112,350 | A * | 5/1992 | Civerchia et al. | 606/107 |
| 5,171,318 | A | 12/1992 | Gibson et al. | 623/5 |
| 5,258,024 | A * | 11/1993 | Chavel et al. | 623/5.16 |
| 5,282,851 | A * | 2/1994 | Jacob-LaBarre | 623/6.56 |
| 5,374,515 | A | 12/1994 | Parenteau et al. | 435/1 |
| 5,458,816 | A * | 10/1995 | Ebner et al. | 261/64.1 |
| 5,458,819 | A * | 10/1995 | Chirila et al. | 264/1.7 |
| 5,580,929 | A | 12/1996 | Tanaka et al. | |
| 5,656,210 | A * | 8/1997 | Hill et al. | 264/2.6 |
| 5,660,692 | A * | 8/1997 | Nesburn et al. | 204/157.68 |
| 5,716,633 | A | 2/1998 | Civerchia | 424/428 |
| 5,836,313 | A | 11/1998 | Perez et al. | 128/898 |
| 5,962,005 | A | 10/1999 | Saga et al. | 424/424 |
| 5,976,648 | A * | 11/1999 | Li et al. | 428/34.9 |
| 6,005,160 | A | 12/1999 | Hsiue et al. | |
| 6,224,893 | B1 * | 5/2001 | Langer et al. | 424/423 |
| 6,254,637 | B1 | 7/2001 | Lee et al. | 623/5.14 |
| 6,372,815 | B1 * | 4/2002 | Sulc et al. | 523/106 |
| 6,391,055 | B1 | 5/2002 | Ikada et al. | 623/5.14 |
| 6,645,715 | B1 | 11/2003 | Griffith et al. | 435/1 |
| 6,673,112 | B2 | 1/2004 | Nigam | 623/5.15 |
| 6,689,165 | B2 | 2/2004 | Jacob et al. | 623/5.16 |
| 6,846,875 | B2 * | 1/2005 | Pennings et al. | 524/557 |
| 6,960,617 | B2 * | 11/2005 | Omidian et al. | 521/102 |
| 7,279,507 | B2 * | 10/2007 | Hu et al. | 523/108 |
| 2001/0044482 | A1 * | 11/2001 | Hu et al. | 523/106 |
| 2002/0007217 | A1 * | 1/2002 | Jacob et al. | 623/5.16 |
| 2003/0022216 | A1 * | 1/2003 | Mao et al. | 435/6 |
| 2003/0100666 | A1 * | 5/2003 | DeGroot et al. | 524/555 |
| 2004/0049268 | A1 | 3/2004 | Noolandi et al. | 623/5.14 |
| 2005/0147685 | A1 | 7/2005 | Osada et al. | 424/487 |
| 2007/0005140 | A1 * | 1/2007 | Kim et al. | 623/17.16 |
| 2008/0119930 | A1 * | 5/2008 | Osada et al. | 623/14.12 |
| 2008/0317818 | A1 * | 12/2008 | Griffith et al. | 424/427 |

FOREIGN PATENT DOCUMENTS

WO    WO 03/093337 A1 *    4/2003

OTHER PUBLICATIONS

Gong et al. "Double-Network Hydrogels with Extremely High Mechanical Strength" (2003) Adv. Materials No. 14 pp. 1155-1158.

Cruise, G.M., D.S. Scharp and J.A. Hubbell, Characterization of permeability and network structure of interfacially photopolymerized poly(ethylene glycol) diacrylate hydrogels. Biomaterials, 1998. 19(14): p. 1287-94.

Padmavathi, N.C. and P.R. Chatterji, Structural characterization and swelling behavior of poly(ethylene glycol) diacrylate hydrogels. Macromolecules, 1996. 29: p. 1976-1979.

Merrett, K., C.M. Griffith, Y. Deslandes, G. Pleizier, and H. Sheardown, Adhesion of corneal epithelial cells to cell adhesion peptide modified pHEMA surfaces. J Biomater Sci Polym Ed, 2001. 12(6): p. 647-71.

Houseman, B.T. and M. Mrksich, The microenvironment of immobilized Arg-Gly-Asp peptides is an important determinant of cell adhesion. Biomaterials, 2001. 22(9): p. 943-55.

Hern, D.L. and J.A. Hubbell, Incorporation of adhesion peptides into nonadhesive hydrogels useful for tissue resurfacing. J Biomed Mater Res, 1998. 39(2): p. 266-76.

Matsuda, T., K. Inoue and T. Sugawara, Development of micropatterning technology for cultured cells. ASAIO Transactions, 1990. 36(3): p. M559-62.

Tsuk, A.G., V. Trinkaus-Randall and H.M. Leibowitz, Advances in polyvinyl alcohol hydrogel keratoprostheses: protection against ultraviolet light and fabrication by a molding process. Journal of Biomedical Materials Research, 1997. 34(3): p. 299-304.

Gong et al. Double-Network Hydrogels with Extremely High Mechanical Strength. Adv. Materials 15 (14) 1155-1158, 2003.

Hern et al. Incorporation of adhesion peptides into nonadhesive hydrogels useful for tissue resurfacing. J. Biomed. Materials Research 39(1) 266-276, 1998.

Evans et al. The use of corneal organ culture in biocompatibility studies. Biomaterials 23 1359-1367, 2002.

Carlsson, D.J., F. Li, S. Shimmura, and M. Griffith, Bioengineered corneas: how close are we? Curr Opin Ophthalmol, 2003. 14(4): p. 192-7.

Evans, M.D., G.A. McFarland, R.Z. Xie, S. Taylor, J.S. Wilkie, and H. Chaouk, The use of corneal organ culture in biocompatibility studies. Biomaterials, 2002. 23(5): p. 1359-67.

Mann, B.K., A.S. Gobin, A.T. Tsai, R.H. Schmedlen, and J.L. West, Smooth muscle cell growth in photopolymerized hydrogels with cell adhesive and proteolytically degradable domains: synthetic ECM analogs for tissue engineering. Biomaterials, 2001. 22: p. 3045-3051.

* cited by examiner

Figure 7 structural regions example peptides aminooxy modified peptide azidobenzamido modified peptide

ARTIFICIAL CORNEAL IMPLANT

FIELD OF THE INVENTION

The invention relates to artificial corneas and corneal implants. More particularly, the invention relates to artificial corneal implants based on double network hydrogels.

BACKGROUND OF THE INVENTION

It is estimated that there are 10 million people worldwide who are blind due to corneal diseases (See e.g. Carlsson et al. (2003) in a paper entitled "*Bioengineered corneas: how close are we?*" and published in "*Curr. Opin. Ophthalmol.* 14(4): 192-197"). Most of these will remain blind due to limitations of human corneal transplantation. The major barriers for treating these patients are corneal tissue availability and resources, particularly for people in developing countries. To have corneas available for transplantation, a system of harvesting and preserving them must be in place. This requires locating potential donors, harvesting the tissue within several hours of death, preserving the tissue, and shipping it to the appropriate facility within one week. Patients who have had refractive surgery may not be used as donors. Therefore, a shortage of corneas may occur in the future, even in developed countries, as the number of patients undergoing refractive surgery increases. Even among patients who are fortunate to receive a corneal transplant, a significant number will develop complications that will result in the loss of vision. The most common complications are graft rejection and failure and irregular or severe astigmatism. In successful cases, the improvement in vision may take many months following the surgery due to graft edema and astigmatism.

A biocompatible artificial cornea with tissue integration and epithelialization can replace the need for a human cornea and provide excellent surgical outcomes. Such an artificial cornea can eliminate the risk of corneal graft rejection and failure, as well as astigmatism, and enable rapid visual recovery. An artificial cornea will ensure an unlimited supply for transplantation anywhere in the world, without the resources required of an eye tissue bank, and eliminate the concern for human cornea shortages due to refractive surgery. Moreover, the technology developed for the artificial cornea can also be applied to the treatment of refractive errors, such as nearsightedness. Through a procedure known as epikeratoplasty, a thin polymer can be attached to the cornea to change the refractive index. A biocompatible epithelialized onlay, placed over the cornea, has an advantage over current technology of laser in situ keratomileusis (LASIK), which requires irreversible corneal tissue removal.

It would be desired to develop an artificial cornea that supports a stable epithelialized surface. Multilayered, stratified epithelial cells would serve as a protective barrier against infections and prevent destructive enzymes from gaining access to the device-cornea interface. The critical requirements for epithelial support of the device are a biocompatible surface for epithelial cellular adhesion and good permeability of glucose and nutrients through the device to support the adherent cells. Other important characteristics of an artificial cornea include optical clarity, biocompatibility, good mechanical strength, ease of implantation, affordability, and allowance for clinical follow-up of intraocular pressure.

Accordingly, it would be considered an advance in the art to develop an artificial cornea encompassing these desirable requirements or characteristics.

SUMMARY

The present invention provides materials that can be applied as implants designed to artificially replace or augment the cornea, such as an artificial cornea, corneal onlay, or corneal inlay (intrastromal lens). The artificial corneal implant includes a double network hydrogel with a first network interpenetrated with a second network. The first network and the second network are based on biocompatible polymers. At least one of the network polymers is based on a hydrophilic polymer. The double network of the invention is characterized by several factors. For instance, the first network is polymerized from macromonomers and the second network is polymerized from monomers, with a molar ratio of the first network macromonomers to the second network monomers lower than $1/100$. In another embodiment, the molar ratio of the first network macromonomers to the second network monomers is between $1/100$ and $1/2000$. Another factor relates to the weight ratio between the first network and the second network, which is in the range of $1/5$ to $3/7$.

The first network could be based on a poly(ethylene glycol) (PEG), poly(2-hydroxyethyl methacrylate) (PHEMA), collagen, hyaluronan hydrogel, poly(vinyl alcohol) (PVA) or derivatives thereof. The second network could be based on poly(acrylic acid) (PAA), poly(acrylamide) (PAAm), poly (methacrylic acid) (PMAA), poly(2-acrylamido-2-methyl-propanesulfonic acid) (PAMPS), poly(2-hydroxyethyl methacrylate), poly(2-hydroxyethyl acrylate) or derivatives thereof.

In one example, the first network is a poly(ethylene glycol)-diacrylate and the second network is a polyacrylic acid (PAA), whereby the concentration of polyacrylic acid is in the range of 30% (v/v) to 50% (v/v). In this example, the poly (ethylene glycol) (PEG) could have a molecular weight of 3400 Da or higher, or more specifically a molecular weight in the range of 3400 Da to 14000 Da.

The artificial cornea or implant of the invention further has epithelialization promoting biomolecules that are covalently linked to the surface of the double network hydrogel using an azide-active-ester chemical linker. In one embodiment, the biomolecules are linked using a 5-azido-2-nitrobenzoic acid N-hydroxysuccinimide ester or a derivative thereof. Examples of biomolecules are e.g. collagen, fibronectin, and laminin, amino-acids, carbohydrates, lipids, and nucleic acids. Corneal epithelial cells or cornea-derived cells are adhered to the biomolecules. The double network has a physiological diffusion coefficient to allow passage of nutrients to the adhered cells. More specifically, the physiological diffusion coefficient is in the range of $10^{-5}$ cm$^2$/sec to $10^{-7}$ cm$^2$/sec.

BRIEF DESCRIPTION OF THE DRAWINGS

The present invention together with its objectives and advantages will be understood by reading the following description in conjunction with the drawings, in which.

DETAILED DESCRIPTION

1. Double Network Hydrogel

Figure 1:
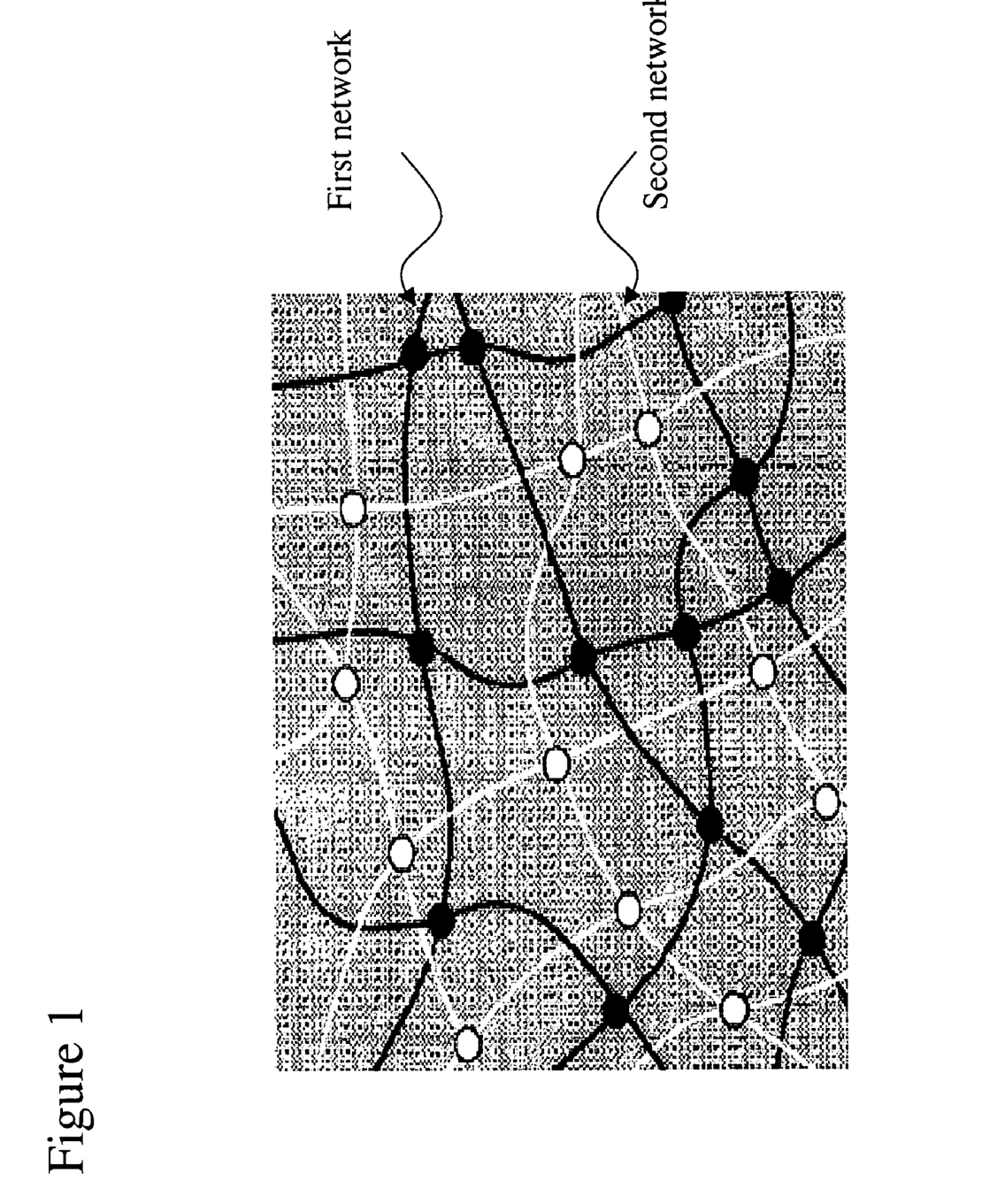
FIG. 1 shows a schematic illustration of a randomly cross-linked double-network (white and black lines represent first network and second networks, respectively).

The artificial cornea includes a double network hydrogel in which a first cross-linked network is synthesized and then a second network is synthesized in the presence of the first. FIG. 1 shows a schematic example of a double-network structure with the intimate interpenetration of two cross-linked networks. Since there is no chemical bonding between the two component networks, each network can retain its own properties while the proportion of each network can be varied independently. Such a double network structure is e.g. capable to swell in water without dissolving and exhibits high mechanical strength as well as high water content, allowing for diffusion of nutrients (See Gong et al. (2003) in a paper entitled "*Double-network hydrogels with extremely high mechanical strength*" and published in "*Advanced Materials* 15(14):1155-1158 for a reference to mechanical strength of double network hydrogels.

For the purposes of the present invention, the double network hydrogel can be comprised of two biocompatible polymers with at least one of these polymers being hydrophilic. Examples of a first network polymer are poly(ethylene glycol) (PEG), poly(2-hydroxyethyl methacrylate) (pHEMA), collagen, hyaluronan hydrogel, poly(vinyl alcohol) (PVA), equivalents thereof, or derivatives thereof. Examples of a second network polymer are poly(acrylic acid) (PAA), poly (methacrylic acid) (PMAA), poly(acrylamide) (PAAm), poly (2-acrylamido-2-methylpropanesulfonic acid) (PAMPS), poly(2-hydroxyethyl methacrylate), poly(2-hydroxyethyl acrylate), equivalents thereof, or derivatives thereof. Any combination of the described first and second network polymers can be used to induce a double network structure of the described composition. The following description refers to an exemplary embodiment of a double network hydrogel with PEG as a first network polymer and PAA as a second network polymer.

In one embodiment, the polymer polyethylene glycol (PEG) is used as the first network. PEG is known to be biocompatible, soluble in aqueous solution, and can be synthesized to give a wide range of molecular weights and chemical structures. The hydroxyl end-groups of the bifunctional glycol can be modified into photo-crosslinkable acrylate end-groups, converting the PEG polymer to PEG-diacrylate polymer. Adding a photoinitiator to a solution of PEG-diacrylate in water and exposing to UV light results in the crosslinking of the PEG-diacrylate, giving rise to a PEG-diacrylate hydrogel. Polymerizing a second network inside the first network will give rise to the double-network structure. The second network composition is typically different from the first. Polymerizing double-network structures by UV light has the additional advantage that it will enable the use of transparent molds to form artificial corneas of desired shape.

To optimize mechanical and other properties of the double network hydrogel, a variety of acrylic based monomers such as acrylamide, 2-acrylamido-2-methylpropanesulfonic acid, acrylic acid, and methacrylic acid and their derivatives can be used in the synthesis of the second network. In one embodiment, poly(acrylic acid)(PAA) hydrogel was used as the second network. PAA is anionic, containing carboxyl groups that become ionized at pH value above the pK$_a$ of 4.7. When the carboxyl groups are ionized, their fixed ions repel one another, leading to further swelling. Therefore hydrogel prepared from PAA exhibited higher equilibrium swelling as pH and AA (acrylic acid) content are increased, which is consistent with the PEG-DA/PAA double network hydrogel of the present invention.

More specifically, the double-network hydrogel can be synthesized by a (two-step) sequential network formation technique based on UV initiated free radical polymerization. A precursor solution for the first network can be made of purified PEG-DA dissolved in phosphate buffered saline (PBS) solution with 2,2-dimethoxy-2-phenylacetophenone (DMPA) as the UV sensitive free radical initiator. The solution can be cast in a mold (e.g. 2 cm in diameter and 250 micrometers in height), covered with glass plates, and reacted under a UV light source at room temperature. Upon exposure, the precursor solution will undergo a free-radical induced gelation and become insoluble in water.

To incorporate the second network, the PEG-based hydrogels are removed from the mold and immersed in the second monomer solution, such as acrylic acid, containing DMPA as the photo-initiator and triethylene glycol dimethacrylate (TEGDMA) as the cross-linking agent for 24 hours at room temperature. The swollen gel is then exposed to the UV source and the second network will be polymerized inside the first network to form a double-network structure. Other monomer candidates for second network such as acrylic acid derivatives, methacrylic acid and its derivatives, acrylamide, or 2-acrylamido-2-methylpropanesulfonic acid can be also incorporated into PEG-based hydrogel using same initiator, crosslinking agent and polymerization procedure.

Instead of PEG, other polymeric materials such as poly(2-hydroxyethyl methacrylate) (PHEMA), poly(vinyl alcohol) (PVA), collagen and hyaluronan (HA)-based hydrogel could be used as the first network. Using these other polymer candidates for the first network, double-network hydrogel can be synthesized by the same (two-step) sequential network formation technique.

For example, to prepare double network hydrogel using pHEMA as the first network, pHEMA-based hydrogel could be synthesized by polymerizing a 70/30 (wt/wt) 2-hydroxyethyl methacrylate/distilled water solution containing 0.12 wt % benzoyl peroxide as an initiator. For the gelation, the solution is reacted in a mold at 60° C. for 24 hours. The second monomer candidate, e.g. acrylic acid, acrylamide, methacrylic acid, or 2-acrylamido-2-methylpropanesulfonic acid is incorporated inside pHEMA-based hydrogel to form a double network hydrogel by the same process described above.

When PVA is used as the first network, 10-20% (wt/wt) solution of PVA in water could be prepared at 80 degrees Celsius and cooled to room temperature. Alternatively, a 10-20% (wt/wt) solution of PVA in a 80:20 mixture of dimethyl sulfoxide (DMSO) and water can be heated to 140 degrees Celsius and frozen at −20 degrees Celsius for multiple 24 hour intervals. For PVA crosslinking, a 25% aqueous solution of glutaraldehyde could be combined with 0.01 N sulfuric acid, and a 17% aqueous solution of methanol. This mixture could then be added to the PVA solution and cast in a mold followed by heating at 75 degrees Celsius for 25 minutes. After gelation, PVA-based hydrogel is immersed in the solution of second monomer candidate such as acrylic acid, acrylamide, methacrylic acid, or 2-acrylamido-2-methylpropanesulfonic acid. Using same polymerization process, second network is incorporated inside PVA-based hydrogel to form double network structure.

For the synthesis of double network based on collagen, first, collagen gel could be formed at physiological conditions by mixing 50% type I collagen, 40% 0.1M NaOH, 10% 10× concentrated Hank's buffer salt solution (HBSS), and 0.02% glutaraldehyde (GTA) is added in bulk as a cross-linking agent. Final solution is cast in a mold before the gel solidified. The resultant collagen gel is immersed in solution of second monomer candidate such as acrylic acid, methacrylic acid, derivatives of acrylic acid or methacrylic, acrylamide, or 2-acrylamido-2-methylpropanesulfonic acid. Using same polymerization process, second network is incorporated inside collagen gel.

To prepare double network based on hyaluronan (HA), 230 mg of sodium hyaluronan (NaHA) is mixed with 0.2 M NaOH, pH 13.0, and stirred over ice for 30 minutes. The HA is then crosslinked with 44 μL of divinyl sulfone in a mold to form gel. This HA gel is immersed in solution of second monomer candidate such as acrylic acid, acrylamide, methacrylic acid, or 2-acrylamido-2-methylpropanesulfonic acid. Using same polymerization process, the second network is incorporated inside HA gel.

Key characteristics of hydrogels such as optical clarity, water content, flexibility, and mechanical strength can be controlled by changing various factors such as the second monomer type, monomer concentration, molecular weight and UV exposure time.

Attenuated total reflectance/Fourier transform infrared (ATR/FTIR) spectroscopy can be used to monitor the photopolymerization of the hydrogels. The conversion of C═C bonds from the precursor solution to the hydrogel can be monitored by measuring the decrease in terminal C═C bond stretching (RCH═CH$_2$) at 1635 cm$^{-1}$ before and after UV exposure. Following synthesis, the double-network hydrogel can be washed extensively in distilled water or PBS to achieve equilibrium swelling and to remove any unreacted components. The water content of the hydrogels can be evaluated by measuring the weight-swelling ratio. Swollen gels can be removed from the bath, patted dry, and weighed at regular intervals until equilibrium is achieved. The equilibrium water content (WC) can be calculated from the swollen and dry weights of the hydrogel (See e.g. Cruise et al. (1998) in a paper entitled "*Characterization of permeability and network structure of interfacially photopolymerized poly(ethylene glycol) diacrylate hydrogels*" and published in "*Biomaterials* 19(14):1287-1294"; and Padmavathi et al. (1996) in a paper entitled "*Structural characterization and swelling behavior of poly(ethylene glycol)diacrylate hydrogels*" and published in "*Macromolecules* 29:1976-1979"). All synthesized hydrogels can be stored in sterile aqueous conditions until further use.

A range of PEG-diacrylate (PEG-DA) double-networks with molecular weights from 575 Da to 14000 Da have been synthesized. It was found that the low molecular weight PEG-DA (<3400 Da) gave rise to gels that were opaque or brittle, whereas the hydrogels made from the higher molecular weight PEG-DA (≧8000 Da) were transparent and flexible. In general and also to prevent phase separation, we found that molecular weight of PEG should be at least more than 3400 Da.

In one example, we fixed the concentration of PEG-DA (molecular weight 3400-14000 Da) to 50% (wt/wt) in PBS for the 1$^{st}$ network and changed concentrations of acrylic acid from 15% (v/v) to 60% (v/v). Cross-linking density of double network hydrogel increased as molecular weight of PEG decreased and concentration of acrylic acid increased. We made a mechanically strong and transparent hydrogel when the concentration of acrylic acid was in the range of 30% (v/v) to 50% (v/v). In this range of concentration of acrylic acid, weight ratio of 1$^{st}$ and 2$^{nd}$ network was between about ⅛ to 3/7. It was also found that incorporation of biomolecules into double network hydrogel did not change the physical properties of hydrogel. Osada et al. in U.S. Patent Application 2005/0147685 have described double network structures with a molar ratio of the first monomer ingredient to the second monomer ingredient of ½ to 1/100, with a lower degree of crosslinking for the second monomer ingredient. The double networks according to the present invention, however, have a molar ratio of the first monomer ingredient to the second monomer ingredient of 1/100 to 1/2000. In one embodiment of the present invention, the double networks have a molar ratio of the first network macromonomers to the second network monomers lower than 1/100. In another embodiment of the present invention, the double networks have a molar ratio of the first network macromonomers to the second network between 1/100 and 1/2000.

Figure 2:
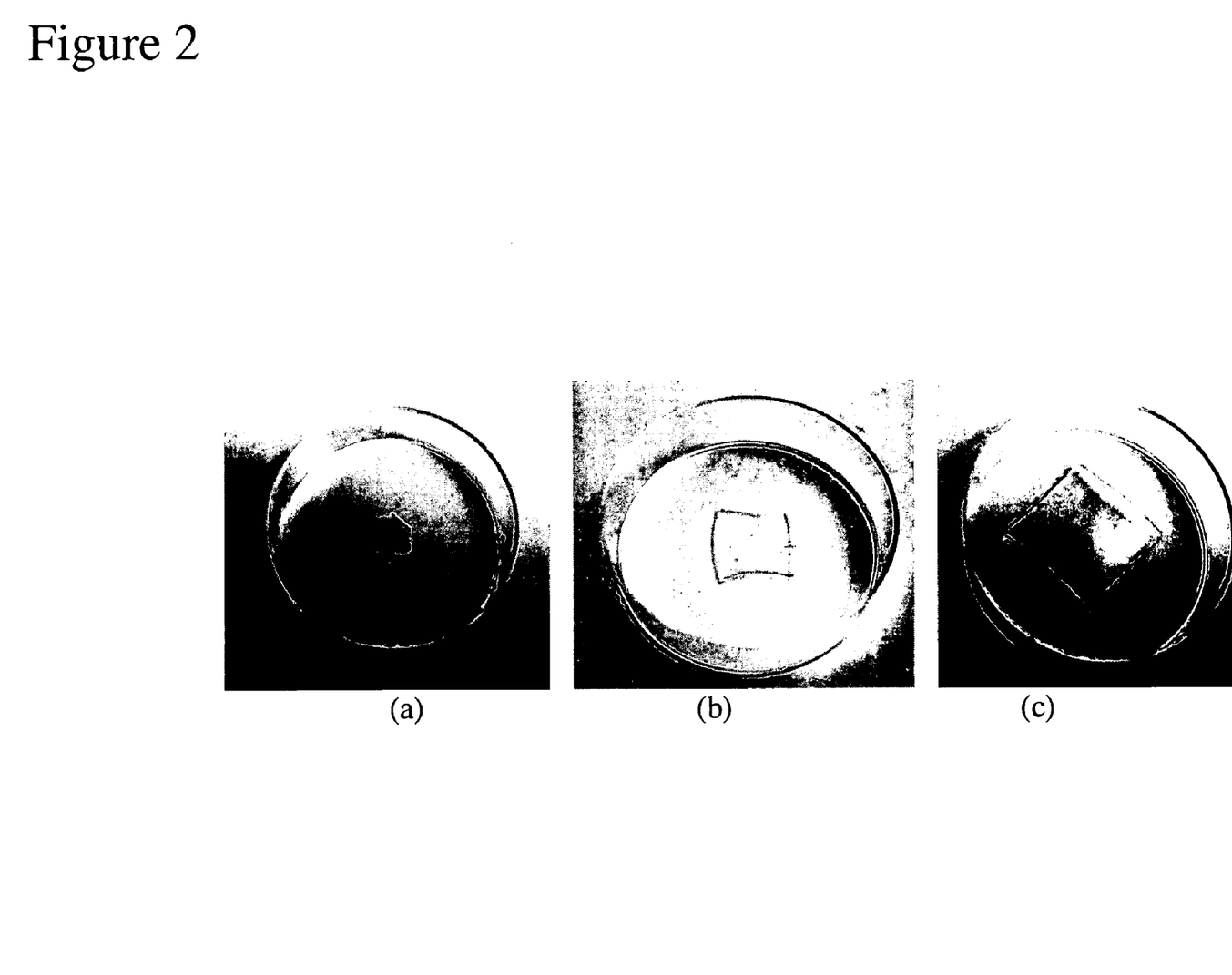
FIG. 2 shows swelling behavior of an exemplary double-network hydrogel composed of PEG and acrylic acid; (a) dried hydrogel, (b) hydrogel exposed to water for 3 min, (c) hydrogel exposed to water for 30 min.
Figure 3:
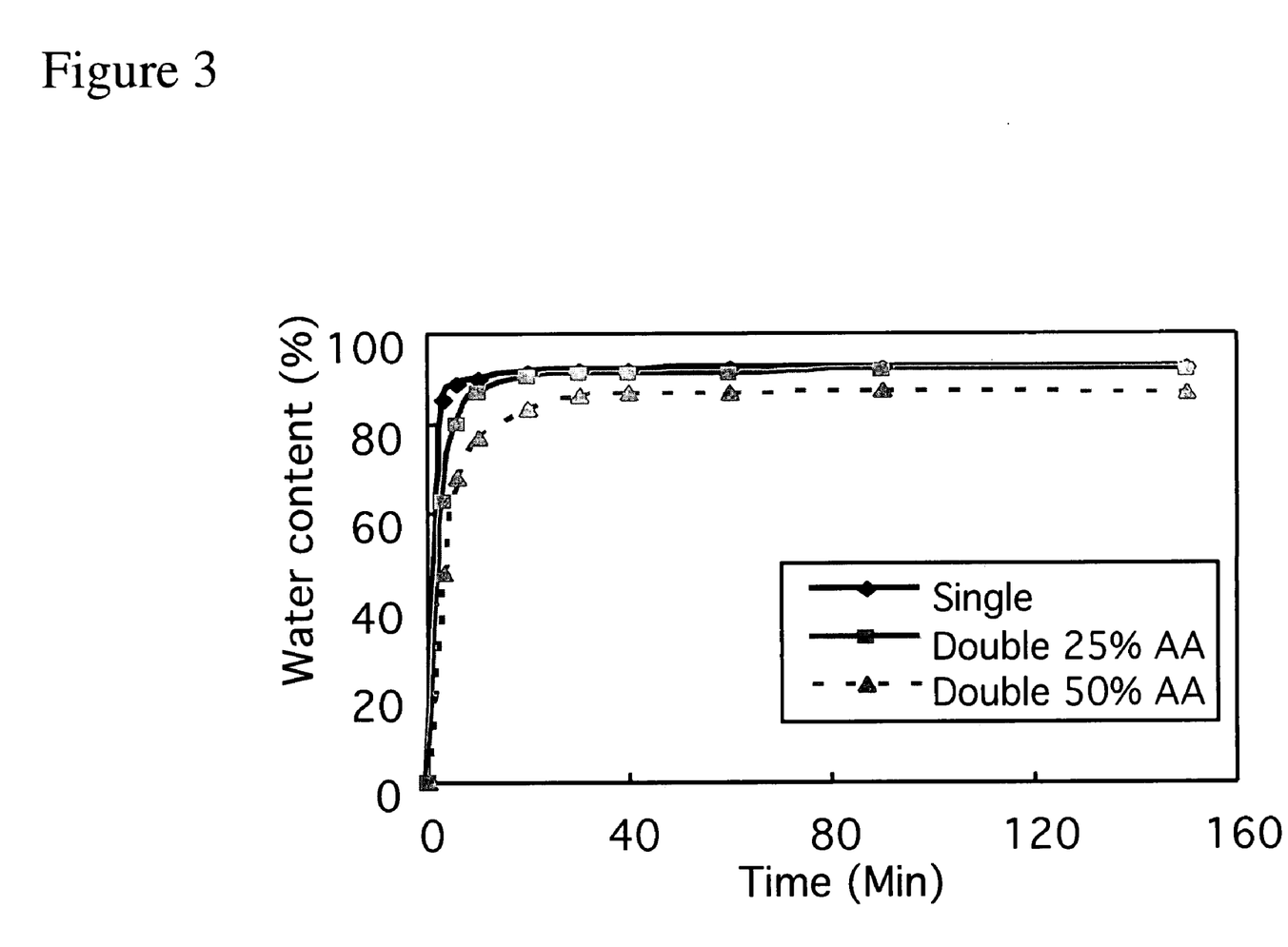
FIG. 3 shows exemplary results of the water content of hydrogels. The double-network is composed of PEG (molecular weight 8,000 Da) and acrylic acid, while the single network is prepared from PEG (molecular weight 8,000 Da).

Based on these results, we have successfully synthesized transparent double-network hydrogels, based of poly(ethylene glycol) (PEG) and acrylic monomers. These double-network hydrogels have better mechanical strength (see next section) compared to single-network (PEG) hydrogels while maintaining a high water content. FIG. 2 shows the time-dependent swelling behavior of a double-network hydrogel composed of PEG and acrylic acid. FIG. 3 shows that the equilibrium water content of the double-network hydrogels can be as high as 90%, which is almost same value as for single-network hydrogels.

2. Mechanical Strength

Figure 4:
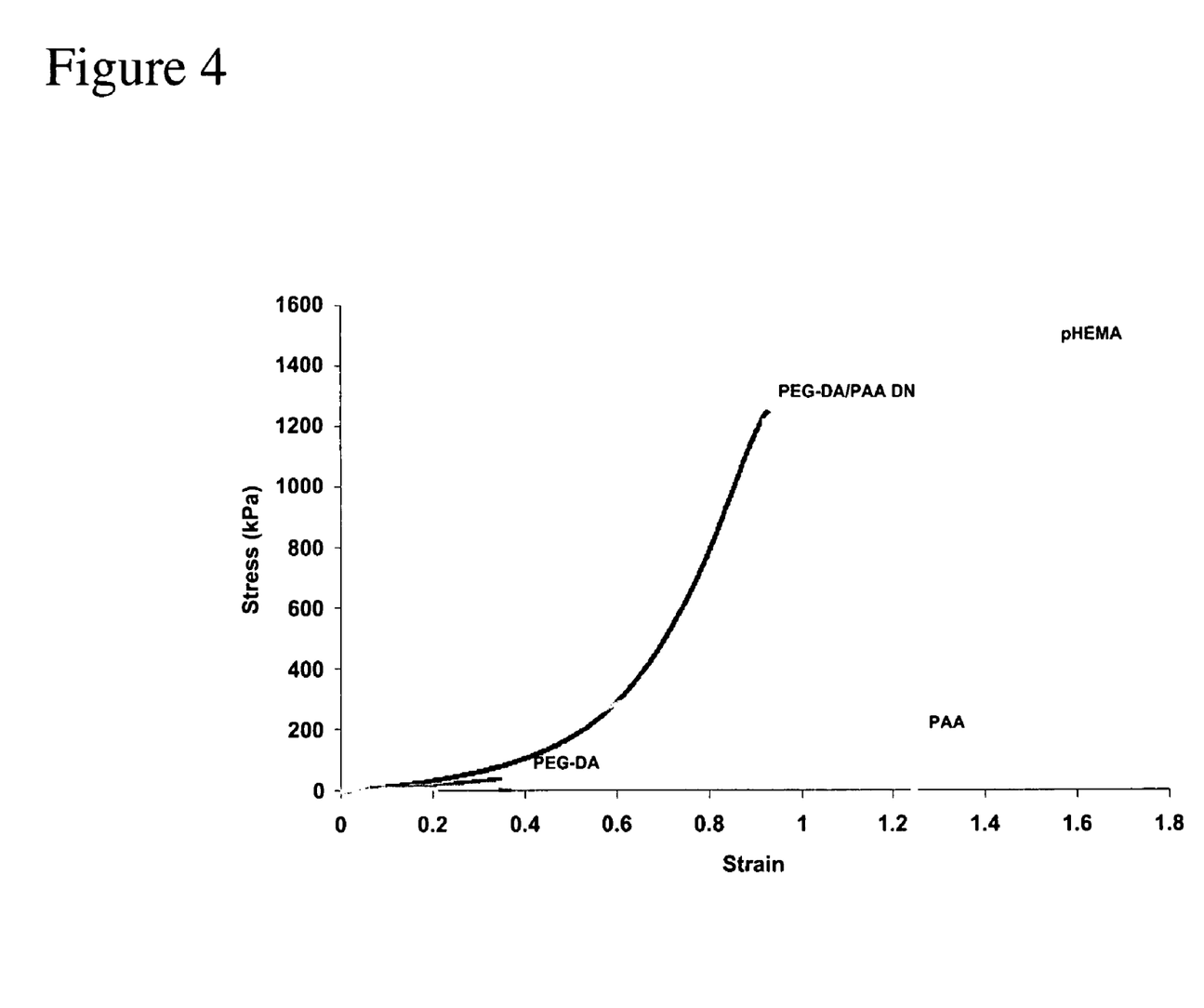
FIG. 4 shows representative stress/strain curves for single-network pHEMA, PEG-DA and PAA, and double-network PEG-DA/PAA hydrogels.

Our extensiometry studies have shown that double-network hydrogels possess a number of important mechanical properties that make them excellent candidates for use as artificial corneas. We have tested double-network hydrogels composed of poly(ethylene glycol)-diacrylate (PEG-DA, 50% w/v in $dH_2O$) and polyacrylic acid (PAA, 50% v/v in $dH_2O$) in the second network. We compared the strength of these double-network gels with single networks of PEG-DA and PAA, as well as the homopolymer pHEMA, a material currently used in keratoprosthesis. The pHEMA hydrogels were synthesized by a previously described protocol (See e.g. Merrett et al. (2001) in a paper entitled "*Adhesion of corneal epithelial cells to cell adhesion peptide modified pHEMA surfaces*" and published in "*J. Biomater. Sci. Polym. Ed.* 12(6):647-71"). The samples were tested on a Bionix 200 MTS Material Testing Apparatus and normalized for thickness. The calculated true stress (kilopascals) and strain (fraction of original length) data are shown in FIG. 4. The combination of PEG-DA and PAA leads to a dramatic improvement in the mechanical strength, consistent with assertions based on compression tests done by Gong et al. (2003) in a paper entitled "*Double-network hydrogels with extremely high mechanical strength*" and published in "*Advanced Materials* 15(14):1155-1158". The effect of double network formation on tensile strength is non-linear, as the maximum strength is many times higher than that of PEG-DA and PAA combined. The DN exhibits a stress-induced stiffening phenomenon that is more characteristic of biological tissues, such as the human cornea. The PEG-DA/PAA DN has a steeper overall stress-strain profile as well as a higher average modulus than the pHEMA hydrogel. Since pHEMA is currently being used in vivo as a keratoprosthesis, it is reasonable to presume that the PEG-DA/PAA DN we have developed would be suitable for such an application as well.

3. Nutrient Permeability

Figure 5:
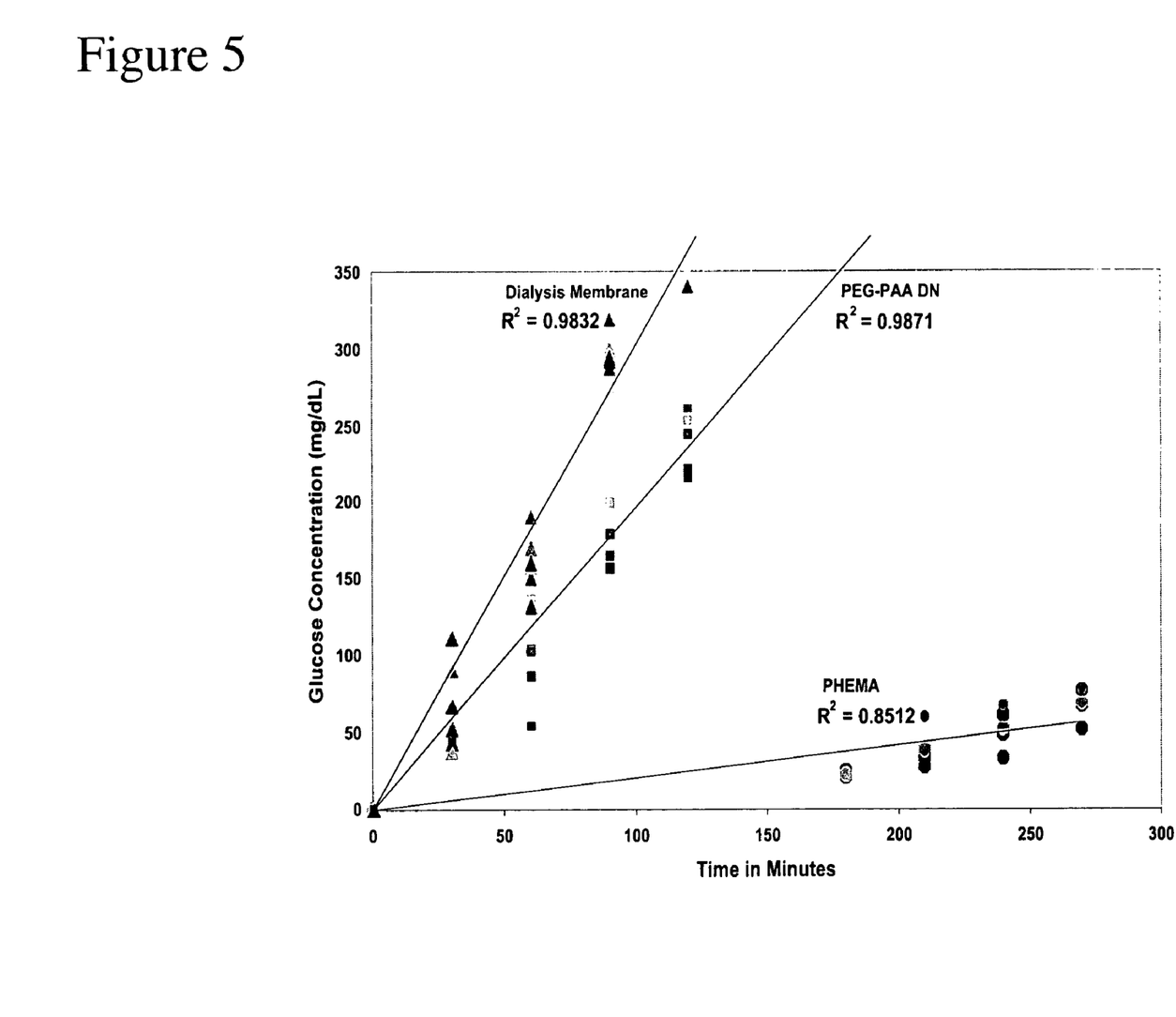
FIG. 5 shows glucose flux across dialysis membrane (triangles), PEG-DA/PAA double-network (squares), and pHEMA (circles). The correlation coefficients for the linear regression fits are indicated. Taking into account the sample thicknesses, this data gives the following average values for the diffusion coefficients: $D_{Dialysis\ Mem.}=10^{-07}$ cm$^2$/s, $D_{PEG-DA/PAA}=9.0\pm1.\ 2\times10^{-07}$ cm$^2$/s, $D_{pHEMA}=2.7\pm0.7\times10^{-08}$ cm$^2$/s.

We studied the glucose permeability across PEG-DA/PAA double-networks, pHEMA homopolymers, as well as human, bovine, and pig corneas in vivo using a modified blind well chamber apparatus developed in our laboratory. In these experiments, non-porous mylar and dialysis membranes (MWCO 12 kD-14 kD) were used as negative and positive controls, respectively. Glucose diffusion coefficients for PEG-DA/PAA (1.10 mm thick) and pHEMA hydrogels (0.250 mm thick) were calculated from data shown in FIG. 5 using Fick's law and taking into account the sample thicknesses. Similarly, glucose diffusion coefficients for human, bovine, and pig corneas were also calculated (data not shown), taking into account corneal thicknesses. Our results indicate that PEG-DA/PAA double-networks ($D_{PEG-DA/PAA}=9.0\pm1.2\times10^{-07}$ $cm^2/s$) are more permeable than pHEMA ($D_{pHEMA}=2.7\pm0.7-10^{-08}$ $cm^2/s$), with a p value of <0.05. This is consistent with the published values of the diffusion coefficient of pHEMA membranes ($D_{pHEMA}\sim10^{-08}$) $cm^2/sec$, which is about two orders of magnitude less than that of the human, bovine and pig corneas we have measured in vitro ($D_{human}\sim10^{-06}$) as well as rabbit corneas ($D_{rabbit}\sim10^{-06}$). This difference is largely due to the lower water content of pHEMA (40%), for the hydration of a material is known to be an important indicator of its permeability. The results from this study indicate that the PEG-DA/PAA DN is able to facilitate adequate passage of glucose to an overlying epithelial cell layer. The threshold of permeability should be between $10^{-05}$-$10^{-07}$ $cm^2/sec$, which is the physiologic range necessary to sustain healthy corneal tissue.

4. Surface Modification

To promote epithelial cell adhesion and proliferation on the nonadhesive hydrogel surface, the surface is modified with biomolecules, such as cell adhesion-promoting proteins such as collagen, fibronectin, and laminin, amino-acids (peptides), carbohydrates, lipids, nucleic acids, or the like. This could be accomplished using two approaches: (1) incorporation of peptides/proteins directly into the polymer during its synthesis and (2) subsequent attachment of peptides/proteins to synthesized hydrogels. The latter approach relies on (a) photoinitiated attachment of azidobenzamido peptides, (b) photoinitiated functionalization of hydrogels with an N-hydroxysuccinimide group followed by reaction with peptides/proteins, and (c) chemoselective reaction of aminooxy peptides with carbonyl-containing polymers. To facilitate stromal keratocyte and fibroblast in-growth into the periphery of the device, extracellular matrix proteins such as collagen, fibronectin, and laminin can be tethered using any of the said methods onto the inner surface of hydrogels made porous (15 μm to 200 μm) produced either by phase-separation, molding, or photolithography.

(1) Preparation of Hydrogel with Incorporated Peptides/Proteins

Figure 6:
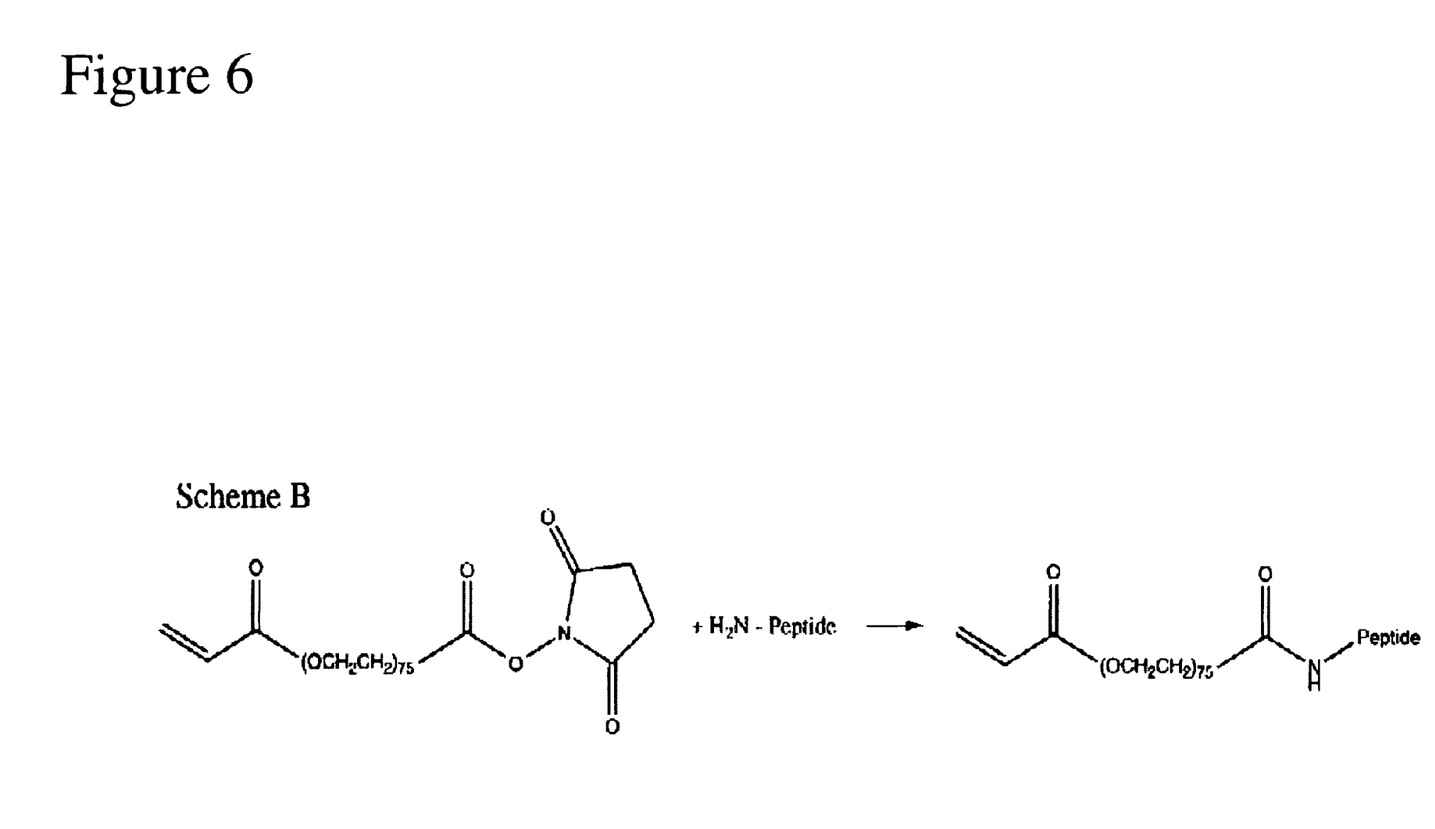
FIG. 6 shows the synthesis of an acrylate-PEG-peptide monomer.

To incorporate cell adhesion peptides directly into double-network hydrogels, the peptides can be reacted with acryloyl-PEG-NHS to form acrylate-PEG-peptide monomers as shown in FIG. 6 (See Mann et al. (2001) in a paper entitled "*Smooth muscle cell growth in photopolymerized hydrogels with cell adhesive and proteolytically degradable domains: synthetic ECM analogs for tissue engineering*" and published in "*Biomaterials* 22:3045-3051"; Houseman et al. (2001) in a paper entitled "*The microenvironment of immobilized Arg-Gly-Asp peptides is an important determinant of cell adhesion*" and published in "*Biomaterials* 22(9):943-955"; and Hem et al. (1998) in a paper entitled "*Incorporation of adhesion peptides into nonadhesive hydrogels useful for tissue resurfacing*" and published in "*J. Biomed. Mater. Res.* 39(2): 266-276"). These peptide-containing acrylate monomers can be copolymerized with other desired acrylates, including PEG-diacrylates, using standard photopolymerization conditions to form peptide-containing hydrogels. The major advantage of this approach is that the peptide is incorporated directly into the hydrogel, and no subsequent chemistry is needed.

An RGD peptide could be used to form an acrylate-PEG-RGD monomer. This monomer could be copolymerized with PEG-DA in forming the first polymer network or with other acrylates in forming the second polymer network. Peptide incorporation could be confirmed by structural characterization of the hydrogels using attenuated total reflectance/Fourier transform infrared (ATR/FTIR) spectroscopy and X-ray photoelectron spectroscopy (XPS). Additional peptides could be used to make new monomers and corresponding hydrogels.

(2) Attachment of Peptides/Proteins to Synthesized Hydrogels

Figure 7:
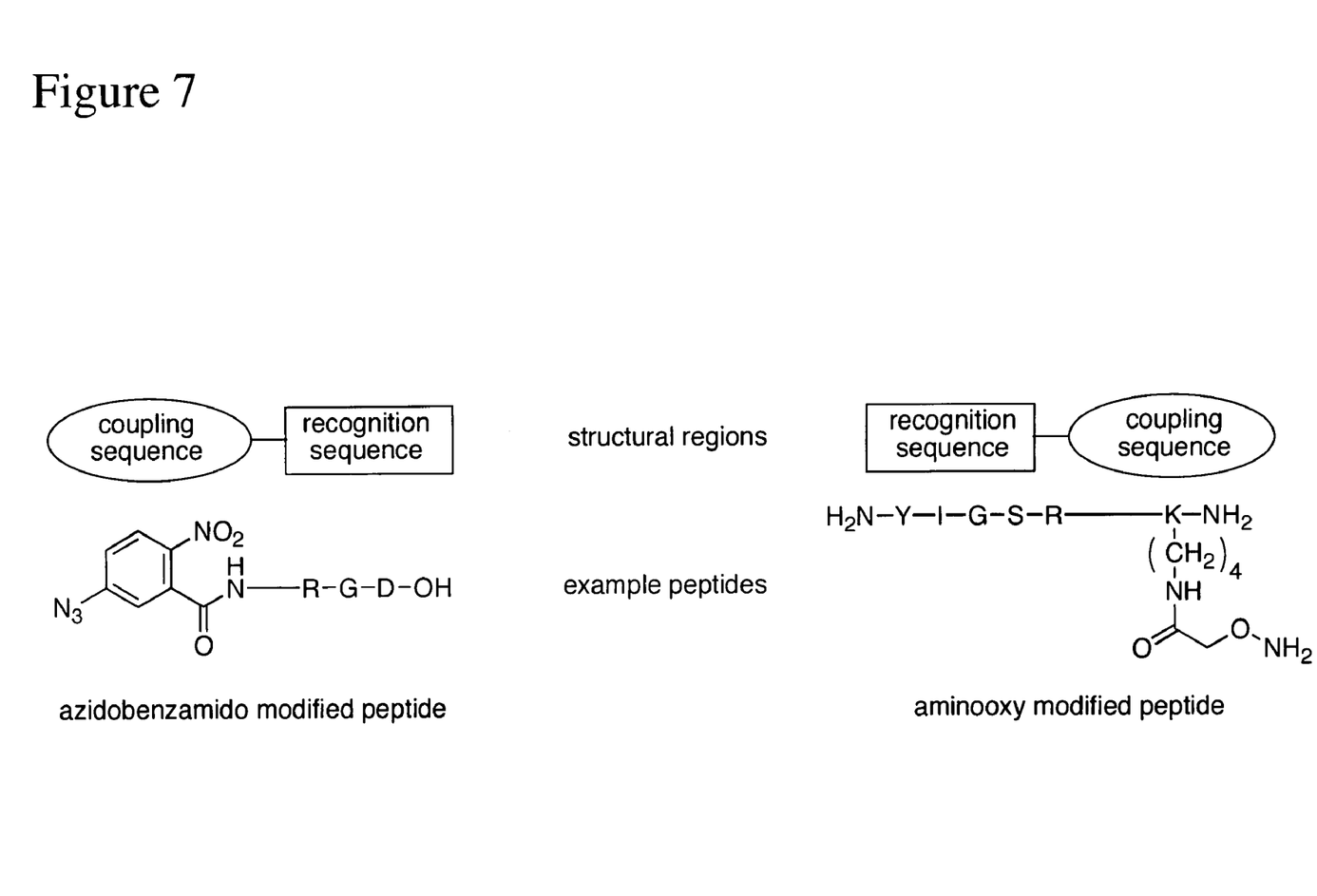
FIG. 7 shows a generic structure and two example peptides that were synthesized.

In this approach, proteins/peptides are attached with the polymers using (a) photoinitiated reaction of azidobenzamido peptides, (b) photoinitiated functionalization of hydrogels with an N-hydroxysuccinimide group followed by reaction with peptides/proteins, and (c) chemoselective reaction of aminooxy peptides with carbonyl-containing polymers. In each method, the peptides can have two structural features: a recognition sequence that promotes cell adhesion and a coupling sequence/residue. The coupling sequence will feature either an azidobenzoic acid moiety or an aminooxy moiety. FIG. 7A shows a generic structure and two example peptides that were synthesized.

Initially, the recognition motifs can be the Laminin-derived sequence YIGSR and the fibronectin-derived sequence RGDS, each of which has been shown to promote corneal epithelial cell adhesion. The coupling moieties can be attached either directly to the N-termini of the peptides or to the amino group of a C-terminal Lys side chain. The peptides can be synthesized by standard, optimized Boc-chemistry based solid phase peptide synthesis (SPPS). Peptide substrates can be purified by HPLC and identified by electrospray ionization mass spectrometry (ESI-MS).

SPPS gives us unparalleled flexibility and control for synthesizing peptides, and it is straightforward to make iterative modifications to independently optimize both the recognition and coupling portions. A major advantage of attachment of peptides after synthesis of the polymers is that it allows combinatorial combination of peptides and polymers to quickly generate large numbers of peptide-decorated hydrogels. For example, five candidate polymers can each be reacted with five peptides to make twenty-five different hydrogels. Moreover, the modular strategy makes it easy to design combinations of different peptides on a single polymer. Multi-peptide surfaces have been proven to be more effective in promoting cell adhesion.

An important aspect of attaching peptides to the surface after polymer synthesis is assessing the success of the attachment. Both analytical and chemical approaches can be used to validate our present methods. Peptide attachment can be confirmed by structural characterization of the hydrogels using ATR/FTIR spectroscopy, XPS and at times amino acid and elemental analysis of the polymers. The attachment strategies can also be validated by using peptides labeled with fluorescent or visible dyes and by use of dynamic contact angle measurements.

(2a) Photoinitiated Reaction of Azidobenzamido Peptides with the Polymers

Azidobenzamido groups react with light (250-320 nm, 5 min) to generate aromatic nitrenes, which insert into a variety of covalent bonds. The peptides could be modified with 5-azido-2-nitrobenzoic acid and 4-azidobenzoic acid. Candidate polymers are incubated in solutions of the desired peptides and then irradiated with UV light to form covalent linkages between the peptides and the polymers. The advantage of this attachment method is that no special functional groups are necessary on the polymer. The disadvantage is the non-specific nature of the attachment, which may make it difficult to control the amount of peptide on the surface. In addition, possible side reactions include nitrene insertions into other peptides rather than the polymers. Moreover, with certain amino acid residues UV radiation is known to create undesirable structures.

(2b) Covalent Attachment of Peptides/Proteins to Polymers Surface Modified by Azide-Active-Ester Linkage.

For the photochemical fixation of peptides/proteins to the hydrogel surfaces, an azide-active-ester chemical containing an photoreactive azide group on one end and an NHS end group (which can conjugate cell adhesion proteins and peptides) on the other end will be used. First, the 5 mg of 5-azido-2-nitrobenzoic acid N-hydroxysuccinimide ester will be dissolved in 1 mL of N,N-dimethylformamide (DMF) (See Matsuda et al. (1990) in a paper entitled "*Development of micropatterning technology for cultured cells*" and published in "*ASAIO Transactions* 36(3):M559-562". This solution will then be evenly spread over hydrogel surfaces and exposed to UV for 5 minutes after the hydrogel surface is air-dried. Upon UV irradiation, the phenyl azide group reacts to form covalent bonds with the hydrogel surface. The irradiated surfaces will be thoroughly rinsed with solvent to remove any unreacted chemicals from the surface. The hydrogels are then incubated for 24 hours in a solution containing the proteins of interest, which react with the exposed NHS end groups.

(2c) Chemoselective Reaction of Aminooxy Peptides with Carbonyl-Containing Polymers Aminooxy groups react chemoselectively under mild conditions (pH 4-5 buffer, room temperature) to form stable, covalent oxime linkages with ketones. We have made ketone-modified hydrogels by using methyl vinyl ketone (MVK) as one of the co-monomers during the polymerization of the second network. The peptides could be modified with aminooxy acetic acid. Candidate hydrogel polymers can be incubated in mildly acidic solutions of the peptide (0.1 M NaOAc, pH 4.0, 24 h) to effect covalent attachment of the peptide to the polymer. Oxime formation has been used extensively for the chemoselective ligation of biomolecules and proceeds extremely well under mild conditions. We have validated the linkage strategy in the context of our hydrogels by synthesizing a conjugate of disperse red 1 and aminooxy acetic acid. Treatment of the MVK hydrogels with this conjugate yielded red-dyed polymers that did not lose their color under the same conditions that removed the color from control polymers treated with disperse red 1 alone.

5. Corneal Cell Growth on Surface Modified Hydrogels

Figure 8:
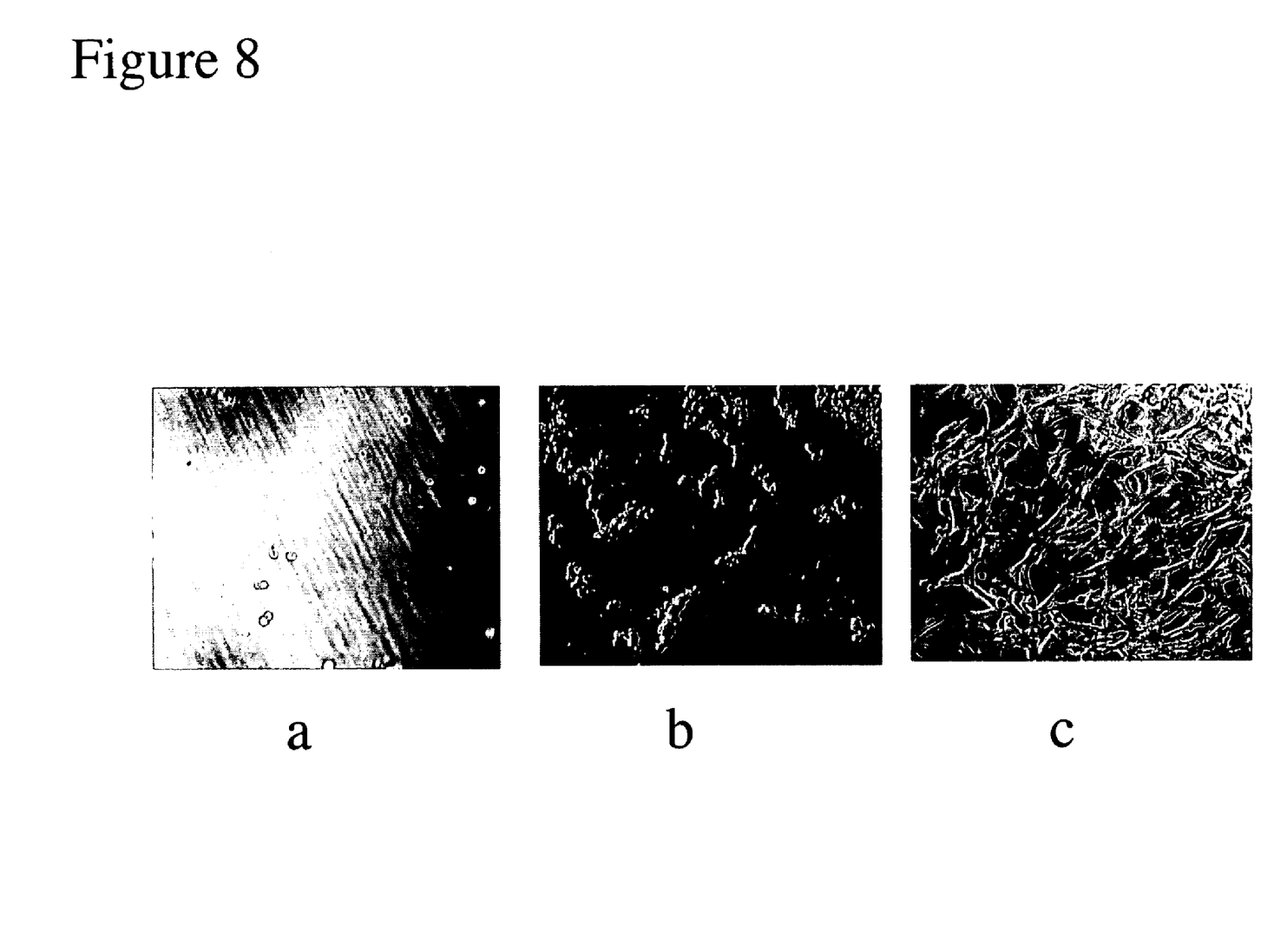
FIG. 8 shows different examples of a corneal cell line derived from corneal epithelium growing on double networks hydrogels. (A) shows cells seeded on PEG-PAA double-network hydrogels after 24 hours. (B) shows corneal cells on PEG-DA/PAA double-network hydrogels incubated in collagen type I, without azide linker, after 24 hours. (C) shows corneal cells on PEG-DA/PAA double-network hydrogels covalently modified with collagen type I via azide-active-ester linkage, after 24 hours.

The effects of modifying PEG-DA, PAA, and PEG-DA/PAA double-network hydrogels with various peptides and proteins in cell cultures have been studied. A rabbit corneal cell line (ATCC number CCL-60) was cultured according to the manufacturer's protocol and seeded onto hydrogels at 100,000 cells/mL within a stainless steel fence to confine the cells to a defined area of 10 mm$^2$. The cells were allowed to incubate in Minimum Essential Medium (MEM) for 24 hours and then photographed using Metamorph software and a Nikon phase contrast inverted microscope. Cells were then seeded on both unmodified and modified hydrogel surfaces conjugated with RGD peptide, collagen type I, fibronectin, and the combination of the three via the described bifunctional azide linker (see infra). In each case, cell adhesion and spreading was observed within 24 to 48 hours. Representative results from these experiments are shown in the photomicrographs FIG. 8. FIG. 8A shows no cell attachment or spreading on an unmodified surface. FIG. 8B also shows poor cell growth on a double-network hydrogel that had been first incubated in collagen type I without the bifunctional azide linker. FIG. 8C, in contrast, shows excellent cell growth and spreading upon a double-network surface covalently modified with collagen type I using the azide linker. Our results show that covalent modification of hydrogel surfaces with peptides and proteins via a bifunctional azide-active-ester linker facilitates cell attachment and spreading upon PEG-DA/PAA double-network hydrogels that otherwise do not allow for cell adhesion.

6. Epithelialization on Surface Modified Double Networks In Organ Culture

Figure 9:
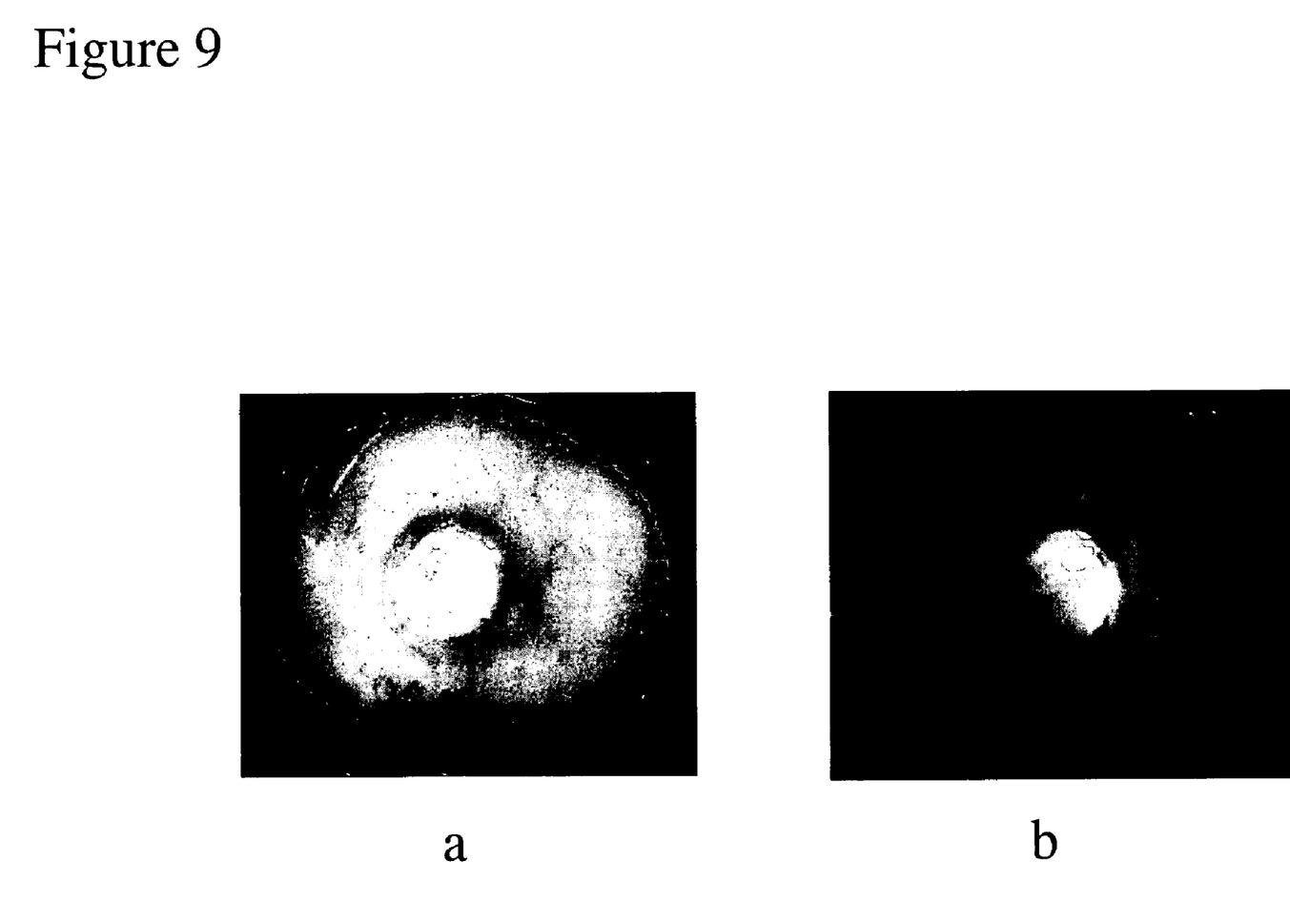
FIG. 9 shows examples of double network hydrogels implants in corneas in organ culture. (A) shows an unmodified PEG-DA/PAA double-network hydrogel implant, showing no epithelial overgrowth at day 5 in organ culture. (B) shows a PEG-DA/PAA double-network hydrogel tethered with collagen type I showing nearly full epithelial overgrowth by day 5 in organ culture.
Figure 10:
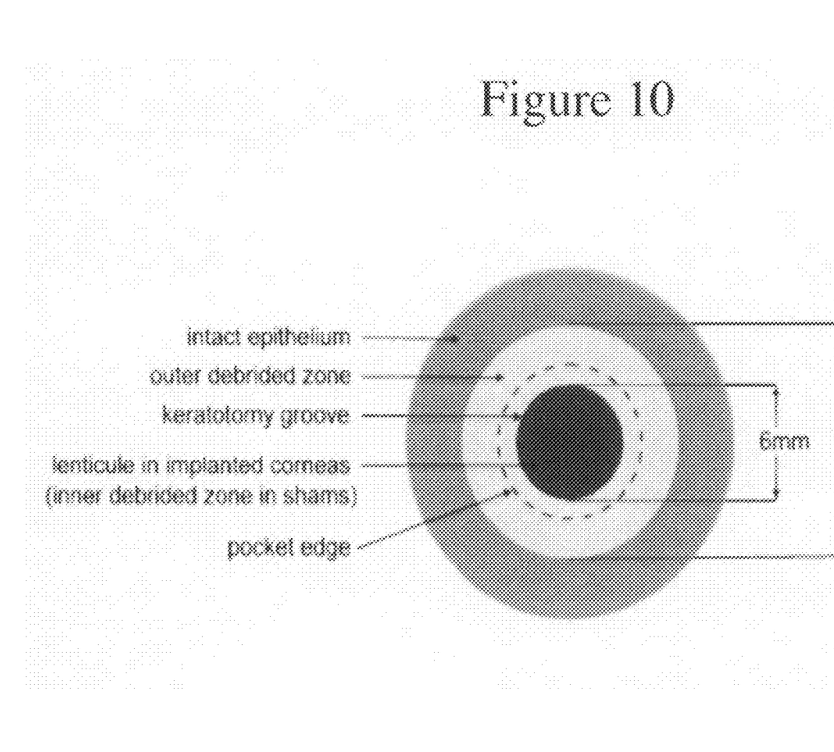
FIG. 10 shows a first schematic diagram (relative to second schematic diagram in FIG. 11) of the surgical procedure by Evans et al. (See Evans et al. (2002) in a paper entitled "*The use of corneal organ culture in biocompatibility studies*" and published in "*Biomaterials* 23(5):1359-1367") that could be utilized for the artificial cornea of the present invention. The corneal implant could either be wedged into the eye or sutured in case the skirt of the implant is sufficiently strong.
Figure 11:
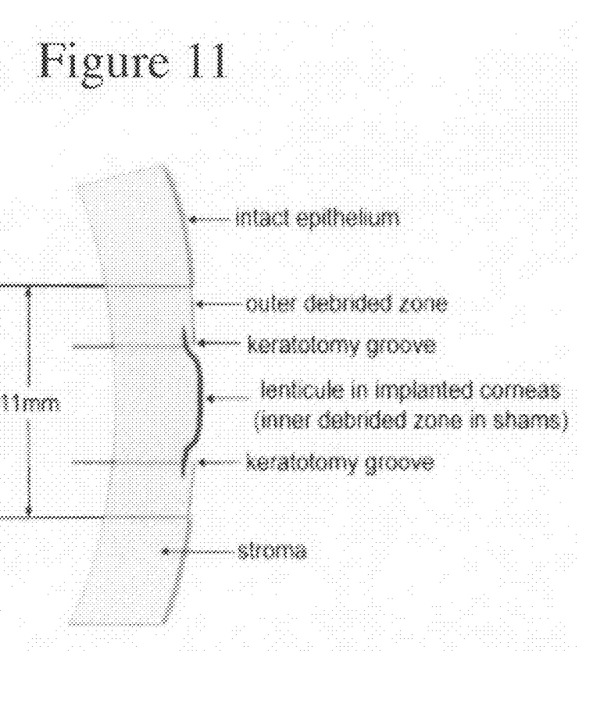
FIG. 11 shows a second schematic diagram (relative to first schematic diagram in FIG. 10) of the surgical procedure by Evans et al. (See Evans et al. (2002) in a paper entitled "*The use of corneal organ culture in biocompatibility studies*" and published in "*Biomaterials* 23(5):1359-1367") that could be utilized for the artificial cornea of the present invention. The corneal implant could either be wedged into the eye or sutured in case the skirt of the implant is sufficiently strong.

FIG. 9 shows the effects of collagen type I on surface epithelialization on PEG-PAA double-networks in bovine organ culture. We implanted PEG-PAA double-network lenticules covalently modified with collagen type I into bovine corneas in vitro according to a known organ culture model (See Evans et al. (2002) in a paper entitled "*The use of corneal organ culture in biocompatibility studies*" and published in "*Biomaterials* 23(5):1359-1367"). The migration and proliferation of epithelial cells across the polymer surface was evaluated at days 0-7 using fluorescein dye to reveal non-epithelialized regions.

Table 1 below compares surface epithelialization results of sham positive control, non-modified and modified hydrogel samples, and polycarbonate negative control. Wound closure occurred in modified PEG-DA/PAA samples (day 5) later than sham samples (day 2.5), while both non-modified PEG-DA/PAA and polycarbonate samples showed no cell overgrowth by day 7.

TABLE 1

| Sample | Surface Modification | Wound Closure Day |
|---|---|---|
| Sham = no implant (positive control) | — | 2.5 |
| Non-Modified PEG-DA/PAA double-network hydrogel | — | No growth by Day 7 |
| Modified PEG-DA/PAA double-network hydrogel | collagen type I | 5 |
| Polycarbonate (negative control) | collagen type I | No growth by Day 8 |

7. UV Protection of Hydrogel

In one embodiment, UV light-absorbing monomers can be incorporated into the synthetic process by co-polymerization. In particular, a benzotriazole monomer (2-(2'methacryloxy-5'-methylphenyl)-benzotriazole (Polysciences, Inc., Warrington, Pa.) and a benzophenone monomer (2-hydroxy-4-acryloxyethoxy)-benzophenone (Cyasorb UV-2098, Cytec Industries, Inc., West Patterson, N.J.) can be used. These have been incorporated into (vinyl alcohol) hydrogels by Tsuk and coworkers (Tsuk et al. (1997) in a paper entitled "*Advances in polyvinyl alcohol hydrogel keratoprostheses: protection against ultraviolet light and fabrication by a molding process*" and published in "*J. Biomed. Mat. Res.* 34(3):299-304"). Once the UV-absorbing monomers have been incorporated into our materials, the light-absorbing capacity can be tested using a spectrophotometer. Finally, the refractive index of all candidate materials can be measured using an automated refractometer (CLR 12-70, Index Instruments, Cambridge, UK).

The present invention has now been described in accordance with several exemplary embodiments, which are intended to be illustrative in all aspects, rather than restrictive. Thus, the present invention is capable of many variations in detailed implementation, which may be derived from the description contained herein by a person of ordinary skill in the art. For example, the hydrogels can be physically modified by phase-separation, or by the use of molds or photolithographic masks during polymerization to yield complex shapes and structures. Separate hydrogels can be fused together by interdiffusion of one monomer along the surface of an existing hydrogel polymer network, with subsequent photopolymerization and crosslinking of the monomer. All such variations are considered to be within the scope and spirit of the present invention as defined by the following claims and their legal equivalents.

What is claimed is:

1. A corneal implant, comprising:
   (a) an interpenetrating double network hydrogel of a first network entangled with a second network, wherein said first network is an entangled network of poly(ethylene) glycol-diacrylate macromonomers covalently bonded to themselves or other of said macromonomers in said first network, wherein each of said poly(ethylene)glycol-diacrylate macromonomers has a molecular weight of 3400 Da or higher, and wherein said second network is based on crosslinked poly(acrylic acid);
   (b) epithelization promoting biomolecules covalently linked to the surface of said double network hydrogel; and
   (c) corneal epithelial cells or cornea-derived cells adhered to said biomolecules.

2. The corneal implant as set forth in claim 1, wherein said first network macromonomers have a molar ratio to said second network monomers lower than 1/100.

3. The corneal implant as set forth in claim 1, wherein said first network macromonomers have a molar ratio to said second network monomers between 1/100 and 1/2000.

4. The corneal implant as set forth in claim 1, wherein the weight ratio between said first network and said second network is in the range of 1/5 to 3/7.

5. The corneal implant as set forth in claim 1, wherein said each of said poly(ethylene)glycol-diacrylate macromonomers has a molecular weight in the range of 3400 Da to 14000 Da.

6. The corneal implant as set forth in claim 1, wherein said biomolecules are linked using an azide-active-ester chemical linker.

7. The corneal implant as set forth in claim 1, wherein said biomolecules are linked using a 5-azido-2-nitrobenzoic acid N-hydroxysuccinimide ester or a derivative thereof.

8. The corneal implant as set forth in claim 1, wherein said biomolecules are selected from the group consisting of collagen, fibronectin, laminin, amino-acids, carbohydrates, lipids, and nucleic acids.

9. The corneal implant as set forth in claim 1, wherein said double network hydrogel has a diffusion coefficient to allow passage of nutrients to said adhered epithelial cells.

10. The corneal implant as set forth in claim 1, wherein said double network hydrogel has a diffusion coefficient in the range of $10^{-5}$ cm$^2$/sec to $10^{-7}$ cm$^2$/sec.

11. A material useful as a artificial cornea, corneal implant, corneal onlay, or corneal inlay, comprising: an interpenetrating double network hydrogel of a first network entangled with a second network, wherein said first network is an entangled network of poly(ethylene)glycol-diacrylate macromonomers covalently bonded to themselves or other of said macromonomers in said first network, wherein each of said poly(ethylene)glycol-diacrylate macromonomers has a molecular weight of 3400 Da or higher, and wherein said second network is based on crosslinked poly(acrylic acid), wherein said first network macromonomers have a molar ratio to said second network monomers lower than 1/100.

12. The material as set forth in claim 11, wherein said first network macromonomers have a molar ratio to said second network monomers between 1/100 and 1/2000.

13. The material as set forth in claim 11, wherein the weight ratio between said first network and said second network is in the range of 1/5 to 3/7.

14. The material as set forth in claim 11, wherein said each of said poly(ethylene)glycol-diacrylate macromonomers has a molecular weight in the range of 3400 Da to 14000 Da.

15. The material as set forth in claim 11, further comprising epithelization promoting biomolecules covalently linked to the surface of said double network hydrogel.

16. The material as set forth in claim 15, wherein said biomolecules are linked using an azide-active-ester chemical linker.

17. The material as set forth in claim 15, wherein said biomolecules are linked using a 5-azido-2-nitrobenzoic acid N-hydroxysuccinimide ester or a derivative thereof.

18. The material as set forth in claim 15, wherein said biomolecules are selected from the group consisting of collagen, fibronectin, laminin, amino-acids, carbohydrates, lipids, and nucleic acids.

19. The material as set forth in claim 11, further comprising epithelization promoting biomolecules covalently linked to the surface of said double network hydrogel and corneal epithelial cells or cornea-derived cells adhered to said biomolecules.

20. The material as set forth in claim 19, wherein said double network hydrogel has a diffusion coefficient to allow passage of nutrients to said adhered epithelial cells.

21. The material as set forth in claim 19, wherein said double network hydrogel has a diffusion coefficient in the range of $10^{-5}$ cm$^2$/sec to $10^{-7}$ cm$^2$/sec.

* * * * *

UNITED STATES PATENT AND TRADEMARK OFFICE
CERTIFICATE OF CORRECTION

PATENT NO. : 7,857,849 B2  
APPLICATION NO. : 11/243952  
DATED : December 28, 2010  
INVENTOR(S) : David Myung Page 1 of 1

It is certified that error appears in the above-identified patent and that said Letters Patent is hereby corrected as shown below:

Title Page, after section (65) "Prior Publication Data" insert Item (60):

--Related U.S. Application Data
(60) Provisional application No. 60/616,262, filed on Oct. 5, 2004. Provisional application No. 60/673,172, filed on Apr. 20, 2005.--

Please add in Column 1, line 2 (before the heading "Field of the Invention") the following paragraph:

CROSS-REFERENCE TO RELATED APPLICATIONS
This application is cross-referenced to and claims the benefit from U.S. Provisional Applications 60/616,262 filed on 10/05/2004 and 60/673,172 filed on 04/20/2005, which are both hereby incorporated by reference.

Signed and Sealed this  
Twenty-second Day of November, 2011

David J. Kappos  
*Director of the United States Patent and Trademark Office*